United States Patent [19]
Graves, Jr. et al.

[11] Patent Number: 5,919,198
[45] Date of Patent: Jul. 6, 1999

[54] DISPOSABLE CARTRIDGE WITH DRIVERS

[75] Inventors: Thomas H. Graves, Jr., Milford; John R. Bittner, Loveland; William G. Bowser, Maineville, all of Ohio; Peter Lau, Taipei, Taiwan; Trevor Speeg, Williamsburg, Ohio

[73] Assignee: Ethicon Endo-Surgery, Inc., Cincinnati, Ohio

[21] Appl. No.: 08/839,853

[22] Filed: Apr. 17, 1997

[51] Int. Cl.⁶ ................................................ A61B 17/04
[52] U.S. Cl. .................... 606/139; 227/176.1; 227/178.1
[58] Field of Search .............................. 606/139; 227/19, 227/175.1, 176.1, 178.1

[56] References Cited

U.S. PATENT DOCUMENTS

| D. 298,967 | 12/1988 | Hunt | D24/27 |
|---|---|---|---|
| D. 337,640 | 7/1993 | Olson | D24/145 |
| 4,043,504 | 8/1977 | Hueil et al. | 227/116 |
| 4,475,679 | 10/1984 | Fleury, Jr. | 227/19 |
| 4,527,724 | 7/1985 | Chow et al. | 227/8 |
| 4,589,582 | 5/1986 | Bilotti | 227/19 |
| 4,633,874 | 1/1987 | Chow et al. | 128/334 |
| 4,805,823 | 2/1989 | Rothfuss | 227/19 |
| 4,892,244 | 1/1990 | Fox et al. | 227/19 |
| 5,106,008 | 4/1992 | Tomkins et al. | 227/178 |
| 5,156,315 | 10/1992 | Green et al. | 227/178 |
| 5,263,629 | 11/1993 | Trumbull et al. | 227/171 |
| 5,332,142 | 7/1994 | Robinson et al. | 227/178 |
| 5,417,361 | 5/1995 | Williams, IV | 227/176 |
| 5,452,837 | 9/1995 | Williamson, IV et al. | 227/176 |
| 5,562,241 | 10/1996 | Knodel et al. | 227/175.1 |

FOREIGN PATENT DOCUMENTS

| 0 140 552 A2 | 5/1985 | European Pat. Off. . |
|---|---|---|
| 0 323 016 A1 | 7/1989 | European Pat. Off. . |
| 0 717 967 A2 | 6/1996 | European Pat. Off. . |

*Primary Examiner*—Gary Jackson
*Attorney, Agent, or Firm*—Louis J. Capezzuto

[57] ABSTRACT

An improved surgical instrument cartridge and method for manufacturing thereof includes providing a cartridge comprising a housing including a surface member and a pair of sidewalls spaced a distance apart from each and connected to the surface member. At least one of the sidewalls has a plurality of slots arranged therein. The slotted sidewall is then deflected such that a plurality of drivers can be placed adjacent the deflected sidewall. Each driver has a tab extending laterally therefrom. The driver tab is inserted directly into the sidewall slot such that each tab is movably confined within each slot and the driver is movable with respect to the slotted sidewalls.

25 Claims, 6 Drawing Sheets

DISPOSABLE CARTRIDGE WITH DRIVERS

FIELD AND BACKGROUND OF THE INVENTION

The present invention relates in general to disposable cartridges for surgical instruments and in particular to a new and useful disposable cartridge and method for manufacturing the cartridge for use in a surgical instrument.

It is a well established practice in the surgical field to utilize surgical instruments for either transecting, fastening or providing hemostasis to tissue, vessels or organs (hereinafter "tissue"). In order to achieve these desired therapeutic effects, it is common practice for a surgeon to utilize a surgical fastening instrument that includes a cartridge containing a plurality of fasteners or clips. Since there are a number of surgical procedures that require multiple firings from a particular surgical fastening instrument, it is common to utilize a cartridge that is disposable such that once the instrument is fired, the cartridge is removed from the instrument and a new cartridge is loaded in its place.

Typically, a disposable fastener cartridge is used in surgical tissue fastening instruments that position the disposable cartridge in an opposed space relationship to an anvil. The anvil provides a fastener forming surface for forming the fired staples or clips thereagainst. In order to achieve the desired therapeutic effects outlined above, tissue is positioned between the cartridge and the anvil of the surgical fastening instrument. These instruments also include a driver assembly that actuates the cartridge for ejecting the fasteners through the tissue for being formed against the anvil.

U.S. Pat. No. 4,633,874 (Chow et al.) discloses a typical surgical fastening instrument which utilizes a disposable fastener cartridge. This instrument is a linear cutter which is generally used in open surgical procedures and includes a disposable cartridge and an anvil. As mentioned above, tissue is placed between the cartridge and the anvil of the linear cutter prior to firing. Upon firing of the cutter, a series of staple rows are formed in the tissue while a cutting knife is advanced between the staple rows for transecting the captured tissue. The cartridge utilized in this type of linear cutter is disposed of once the instrument is fired.

U.S. Pat. No. 5,332,142 (Robinson et al.) discloses a linear cutter which is used for endoscopic surgical procedures. This type of linear cutter is similar to the linear cutter outlined above, however, both the cartridge and the anvil are located at the distal end of an elongated shaft for facilitating tissue fastening and transection in various minimally invasive surgical procedures.

U.S. Pat. No. 4,527,724 (Chow et al.) discloses a linear stapler that is used in open surgical procedures. This type of linear stapler also includes a disposable fastener cartridge and an anvil positioned directly opposite the cartridge. Once tissue has been positioned between the cartridge and the anvil, the cartridge is movably adjusted with respect to the anvil for adjusting the gap between the cartridge and the anvil. Once this instrument is fired, a cutting instrument such as a scalpel may be required to transect the fastened tissue if so desired. This transection occurs by advancing the scalpel blade across the tissue and against the anvil.

All of the instruments referenced above, are utilized in various surgical procedures that may require multiple firings of the instrument. Accordingly, all of these instruments utilize a disposable cartridge having a plurality of fasteners, staples or clips that are stored within the cartridge and deployed from the cartridge upon firing of the instrument. It is greatly appreciated by those of ordinary skill in the surgical field that these cartridges are required to be quite sophisticated in design and construction in order to meet the demanding precisional requirements of the various surgical procedures. It is critical that a disposable fastener cartridge be designed and constructed such that upon firing, the cartridge ejects fasteners that exhibit expected and predicted fastener heights when fired into tissue. Accordingly, it is extremely important that the cartridge exhibit repeatable and predicable performance.

Thus, great care is taken in the design and manufacture of disposable cartridges. Due to the sophistication of the cartridge design, the manufacturing process for these cartridges can be quite rigorous due to the various manufacturing steps that are required. These steps are required to be carried out with great precision and care in order to ensure the quality that is expected from the surgeon and the patient. Accordingly, rigorous specifications are required for both the cartridges design and manufacture in order to prevent misfires, defective deployment of fasteners or jamming of the surgical instrument upon firing. Thus, significant effort and process controls are put into place to ensure that cartridges meet these specifications. As one could imagine, a great deal of resources are required in order to deliver a high quality disposable cartridge.

In a surgical environment in which cost is an extremely important factor, it is imperative that the disposable cartridges have a design and method for manufacturing that is cost effective yet be able to meet rigorous specification requirements. Presently, there is no known surgical fastener cartridge that has a design that supports an efficient and cost effective manufacturing process and that sufficiently meets the precision and quality requirements for use in surgery.

SUMMARY OF THE INVENTION

The present invention is a disposable cartridge for a surgical instrument that fires a plurality of fasteners such as staples or clips.

The cartridge according to the present invention is a housing which comprises a surface member and a pair of sidewalls spaced a distance apart from each other and connected to the surface member. At least one of the sidewalls has a plurality of vertical slots arranged therein. This sidewall is deflectable such that a plurality of drivers can be placed adjacent the slotted sidewall. Each of the drivers that are utilized with the present invention have a tab which extends therefrom which is insertable into a respective slot in the sidewall. Each driver is movable with respect to the slotted sidewall and each tab is movably confined within the slot. A staple is located on each driver and is contained within the cartridge.

The present invention also includes a novel method for manufacturing a disposable cartridge for a surgical fastening instrument comprising providing a cartridge having a surface member and a pair of sidewalls spaced a distance apart from each other and connected to the surface member wherein at least one of the sidewalls has a plurality of slots arranged therein. The slotted sidewall is then deflected and a plurality of drivers are placed adjacent the deflected sidewall. Each driver has a tab whereby each tab is inserted into the respective slot of the deflected sidewall such that each driver is movable with respect to the slotted sidewall. Each tab is movably confined within each slot. Lastly, a staple is loaded into the cartridge by placing a staple on each driver.

It is an object of the present invention to provide a disposable cartridge for a surgical fastening instrument that is simple in construction and cost effective in design.

It is another object of the present invention to provide a disposable cartridge for a surgical fastening instrument that provides a simple and cost effective manufacturing method.

It is another object of the present invention to provide a disposable cartridge for a surgical fastening instrument that allows for predictable fastener heights.

It is another object of the present invention to provide a disposable cartridge for a surgical fastening instrument that provides a high quality and predictable method for manufacturing a cartridge.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
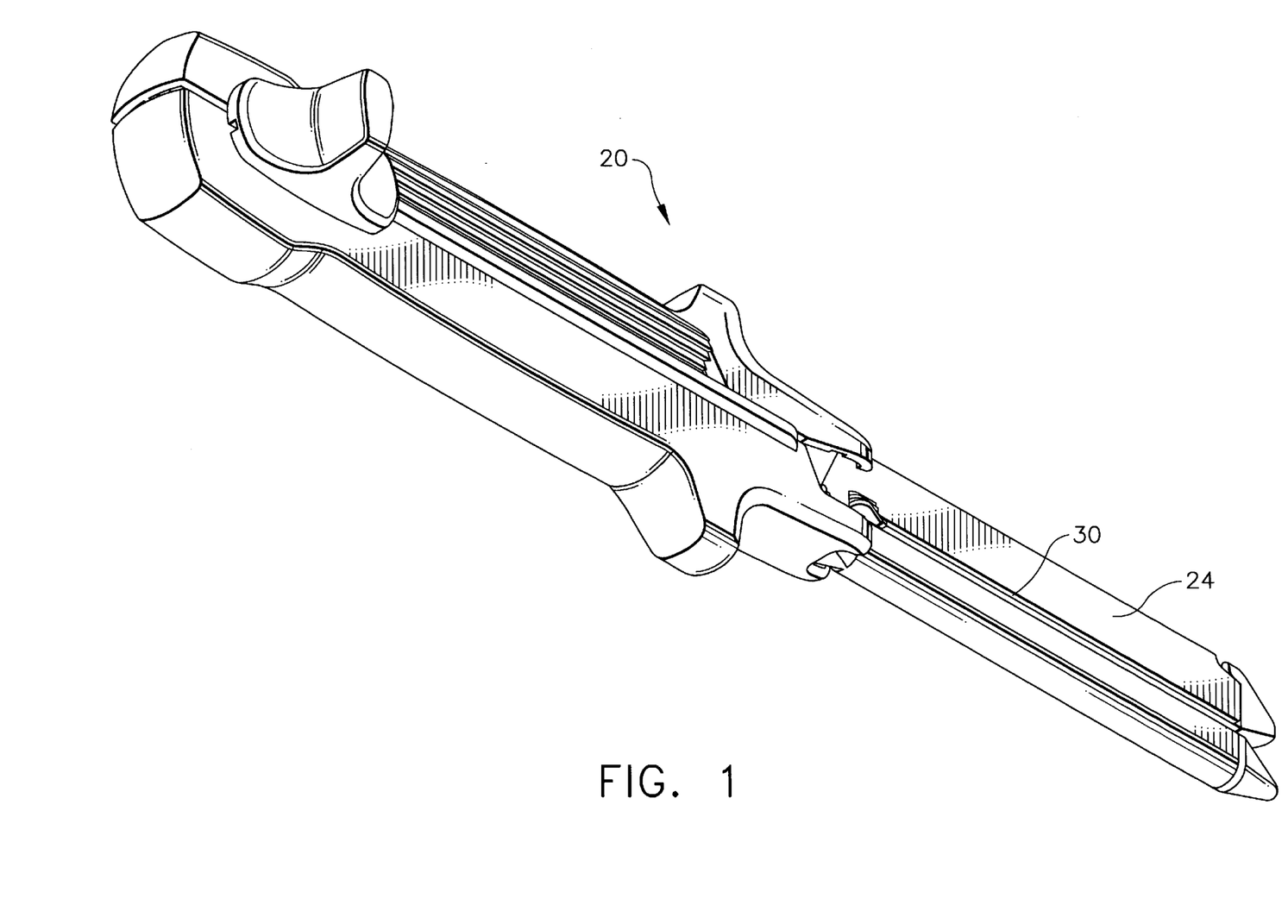
FIG. 1 is a perspective view of a surgical fastening instrument.

The present invention is directed to a disposable cartridge containing a plurality of fasteners or clips that are used in conjunction with a surgical fastening instrument. FIG. 1 illustrates a typical surgical fastening instrument, generally designated 20, which utilizes a cartridge holder 24 for firing a disposable cartridge 30.

Prior Art Cartridge

Figure 3:
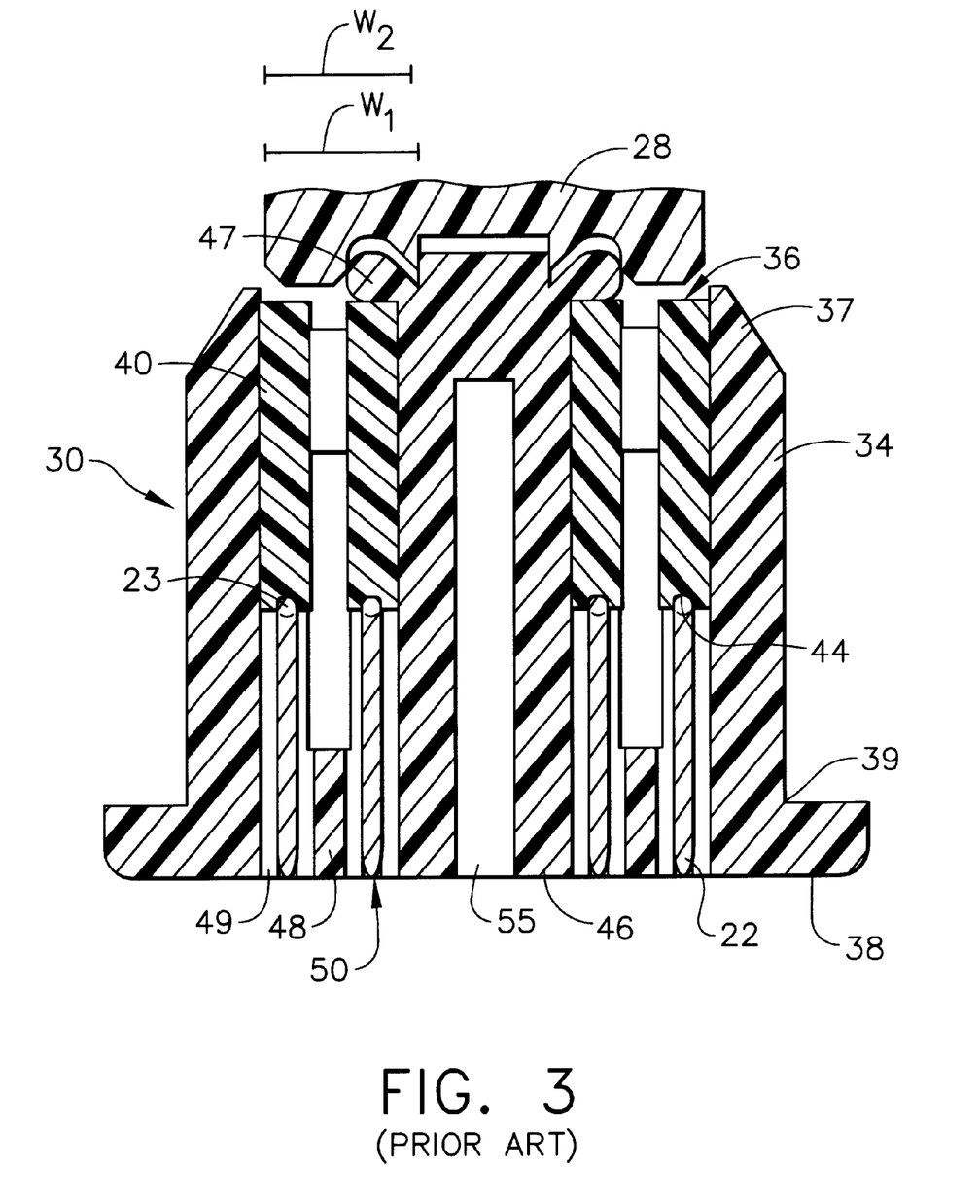
FIG. 3 is a transverse view in section of a prior art fastener cartridge with a pressing tool in fragmentary section used in the manufacture of said cartridge.

A typical disposable cartridge 30, which is known in the prior art, is illustrated in FIG. 3. The cartridge 30 is a housing made of a thermoplastic material and comprises a surface member 38 which is a platform having a plurality of openings or pockets 50 therein. A pair of sidewalls 34 having distal ends 37 are spaced apart from each other and are connected to an underside 39 of the surface member 38 opposite the distal ends 37. Each sidewall 34 vertically extends from the underside 39 of the surface member 38 and are substantially parallel to each other.

A main rib 46 separates sidewalls 34 and is connected to the surface member 38 at the underside 39 of the surface member 38. The main rib 46 also vertically extends from the surface member 38 and is substantially parallel to the sidewalls 34. The main rib 46 also includes a distal end 47 which extends a short distance past the distal ends 37 of the sidewalls 34. A knife slot 55 axially extends through the main rib 46 for accommodating a knife blade (not shown) for those instruments which utilize a cutting knife. These types of instruments are generally known as linear cutters which were described in the Field and Background Section herein.

The surface member 38, the sidewalls 34 and the main rib 46 define a vertical space or driver cavity, generally designated 36, on each side of the main rib 46. Webs 48 are connected to the underside 39 of the surface member 38 and are positioned in each driver cavity 36 at the surface member 38. Guide tracks 49 are included in each driver cavity 36 and lead to the pockets 50. Each pocket 50 is aligned directly with the driver cavities 36.

Drivers 40 are located in each driver cavity 36 and are movable therein. The driver cavities 36 have a width $W_1$ that is slightly larger than a width $W_2$ of the drivers 40. The driver cavity width $W_1$ is sized such that driver width $W_2$ can be easily accommodated for direct insertion or dropping of the drivers 40 into the driver cavities 36. Driver cavity width $W_1$ is larger than the driver width $W_2$ for quick loading of the drivers 40 into the driver cavities 36 which is normally performed by hand during manufacturing of the cartridge 30. Additionally, the driver cavity width $W_1$ permits vertical movement of the drivers 40 in the cavities 36 up until the drivers 40 meet the webs 48 of the cartridge 30.

Drivers 40 also include staple grooves 44 at an upper end of each driver 40 for holding a staple 22 thereon by a crown 23 of each staple 22.

The staple tracks 49 are located adjacent the sidewalls 34, the webs 48 and the main rib 46 respectively for assisting and guiding the staples 22 through the pockets 50 in a linear fashion upon the firing and actuation of the drivers 40.

Prior Art Cartridge Manufacturing Method

The manufacturing method for the prior art cartridge 30 illustrated in FIG. 3 is an extremely time consuming and tedious process that requires very strict manufacturing specifications for the cartridge 30. First, the cartridge is oriented such that the surface member 38 is placed on a flat surface with the distal end 47 of the main rib 46 located in a superior position. Then, the drivers 40 are hand loaded into the cavities 36 by dropping the drivers 40 directly into the cavities 36. As mentioned above, the driver cavity width $W_1$ is sized sufficiently to permit the driver width $W_2$ to be easily accommodated. Accordingly, the drivers 40 can be dropped into the driver cavities 36 without any resistance.

Once the drivers 40 have been hand loaded into the cavities 36, a pressing tool 28 which is usually a heat staking die, having a particular staking pattern embossed thereon, is pressed against the distal end 47 of the main rib 46. Pressing tool 28 is heated to a high temperature such that the plastic material of the main rib distal end 47 can be melted and deformed in the shape of the embossing pattern of the pressing tool 28. During this step of the manufacturing process, an operator ensures that the pressing tool 28 is pressed directly into the main rib distal end 47 thereby causing a substantial portion of the distal end 47 to encroach over the cavities 36 for preventing the drivers 40 from falling out of the cartridge 30. This step is a heat staking step which is a critical step in the manufacturing process. Critical factors which influence this heat staking step are temperature of the pressing tool 28, amount of pressure or force exerted on the main rib distal end 47 by the pressing tool 28, amount of time the pressing tool 28 is left pressed against the main rib distal end 47 and the type of embossing pattern on the pressing tool 28 as well as other influencing factors. Additionally, it would not be uncommon for the pressing tool 28 to be a cold staking die or other type of staking die so long as it could sufficiently deform the main rib distal end 47.

Once the heat staking step has been performed, the staples 22 are loaded into the cartridge 30 such that the staple crowns 23 of the staples 22 are positioned in each groove 44 of the drivers 40.

Once the staples are loaded into the cartridge 30, a shipping tab or staple retainer (not shown) is usually placed over the surface member 38 covering the pockets 50 in order to ensure that the staples 22 are maintained in the cartridge 30 during shipping and handling.

One of ordinary skill in the surgical field can appreciate that there are many problems associated with this known method of disposable cartridge manufacture. As indicated above, the heat staking step is a critical step in the manufacturing process since it is performed with a pressing tool that is heated to a sufficiently high temperature for deforming the main rib distal end 47. As mentioned above, there are strict process parameters such as the amount of heat and the amount of pressure which must be controlled. Any slight variance in these parameters will result in the improper manufacturing of the cartridge 30. Moreover, the shape of the pressing tool 28 is extremely important for ensuring that the main rib distal end 47 is deformed with precision such that an exact amount of material from the main rib distal end 47 can be deformed in order to cover a portion of the cavity 36 without encroaching into the cavity 36 such that it affects the intended positioning or movement of the drivers 40 within the cavities 36. It is critical that the deformed main rib distal end 47 be able to retain the driver 40 in the cavity 36 by blocking a portion of the cavity 36 but should not increase any frictional drag of the driver 40 within the cavity 36. Any increase in frictional drag of the driver 40 with respect to the cavity 36, will have an adverse impact on the functioning of the cartridge 30.

It is very important to have a finished cartridge height that meets specifications such that the cartridge 30 can be properly positioned and fired in the surgical instrument 20 (FIG. 1). Thus, if the pressing tool 28 is not utilized in the exact and prescribed manner, there is a good chance that the cartridge 30 will not fit properly in the cartridge holder 24 of the surgical instrument 20. Any improper alignment of the cartridge 30 within the cartridge holder 24 could lead to a result where the drivers 40 are advanced substantially past the cartridge 30 thereby exceeding their prescribed advancement distance. This is commonly known as an overdrive of the cartridge drivers 40.

Since there are many variables in the prior art manufacturing method described above, there is a high degree of error built into this known cartridge manufacturing process. Accordingly, even for those cartridge manufacturing techniques and processes that are tightly monitored and controlled, there is still a good percentage of cartridges that are manufactured and still fall short of required specifications. These cartridges result in scrap and added cost to the overall manufacturing process. It is estimated that the scrap rate of the known cartridge 30 can be as high as five percent of the total of cartridges produced. As could be expected, these cartridges are never released and result in increased cost to the manufacturer.

Present Invention Cartridge

Referring now to FIGS. 2–6, the present invention is a disposable fastener cartridge, generally designated 30a, for use in the types of surgical instruments mentioned above. The same reference numerals are used to designate like or similar parts to those parts described and illustrated for the prior art cartridge 30 in FIG. 3.

Figure 2:
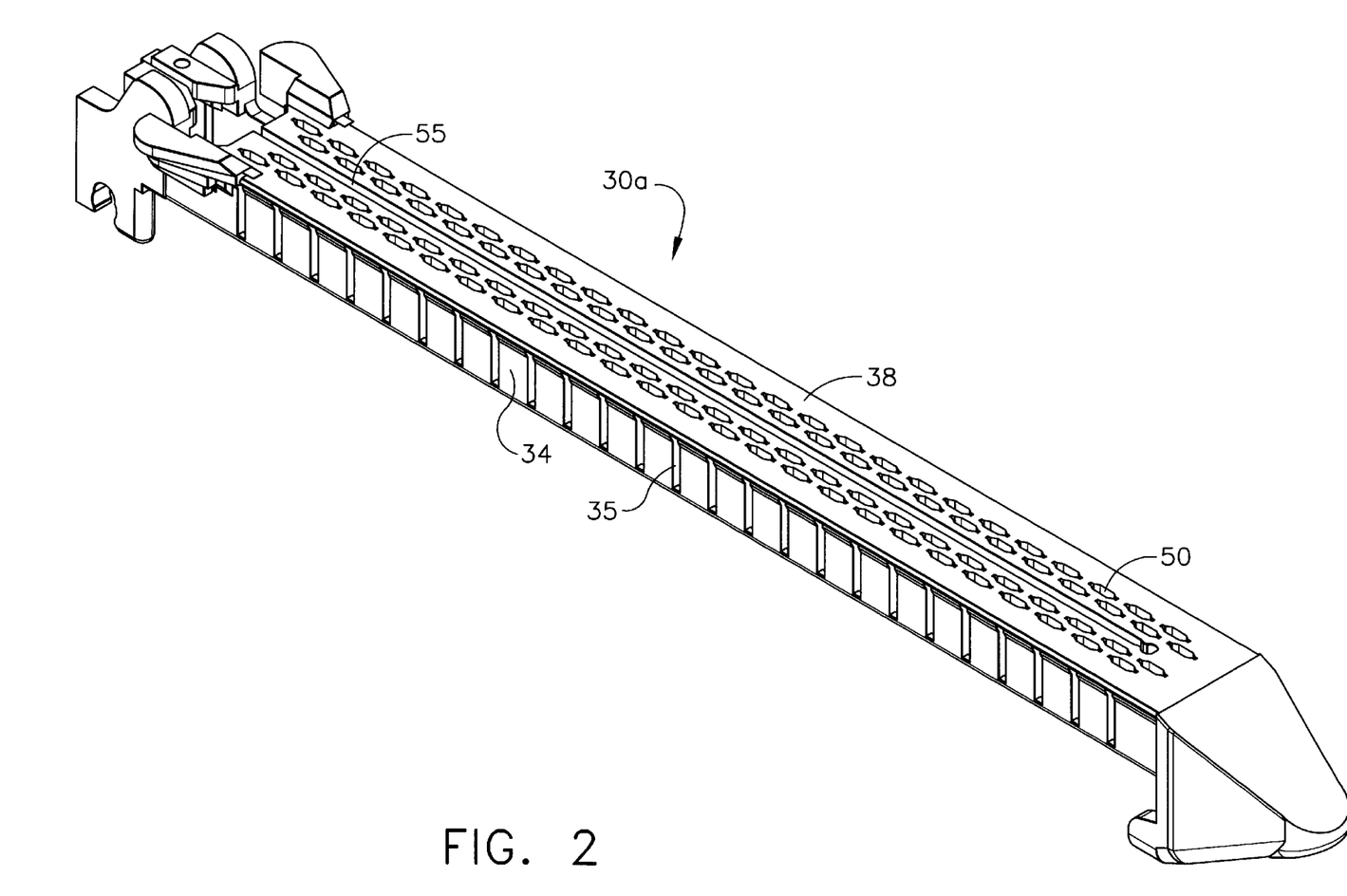
FIG. 2 is a perspective view of a disposable fastener cartridge according to the present invention for use in the surgical fastening instrument of FIG. 1.
Figures 4, 5A:
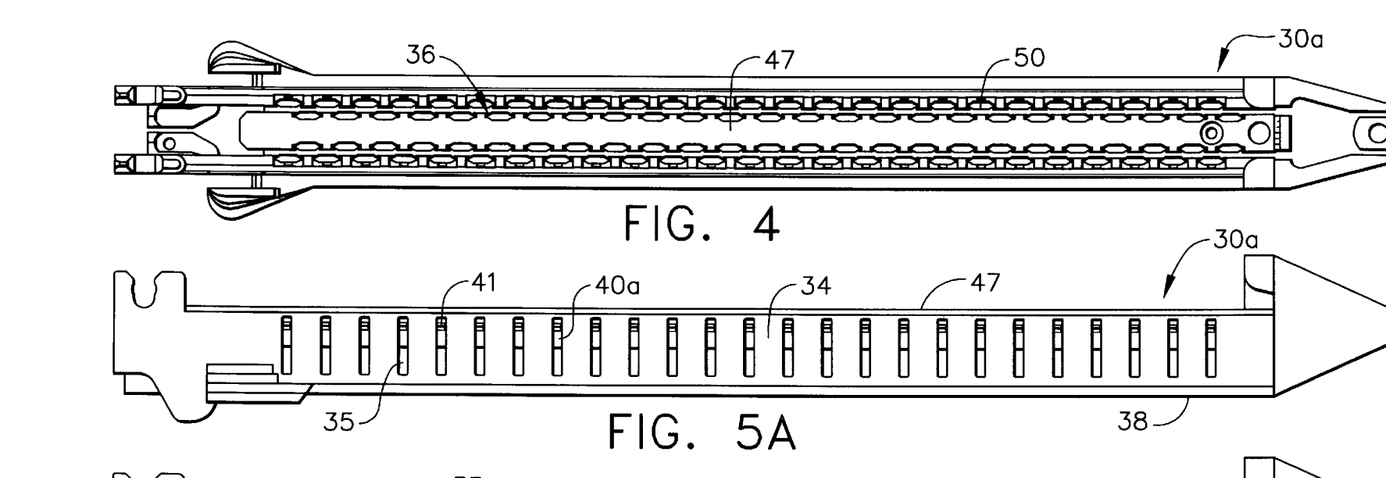
FIG. 4 is a bottom plan view of the preferred fastener cartridge of FIG. 2.
FIG. 5A is a side elevation view of the cartridge of FIG. 4 with the drivers in a pre-fire position.
Figure 5B:
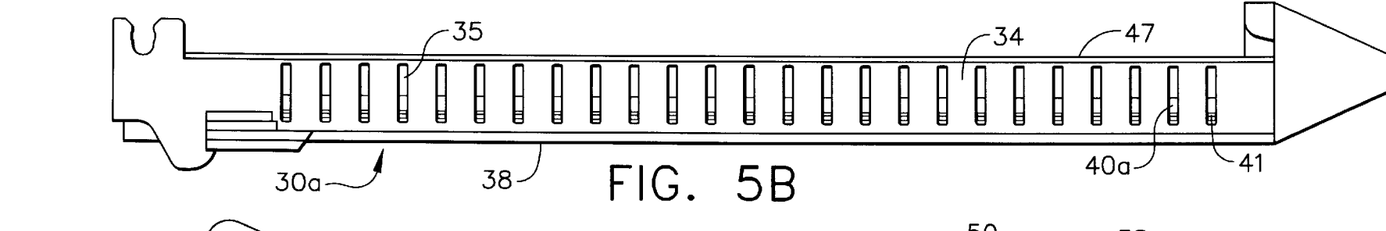
FIG. 5B is a side elevation view of the cartridge of FIG. 4 with the drivers in a fired position.
Figure 6:
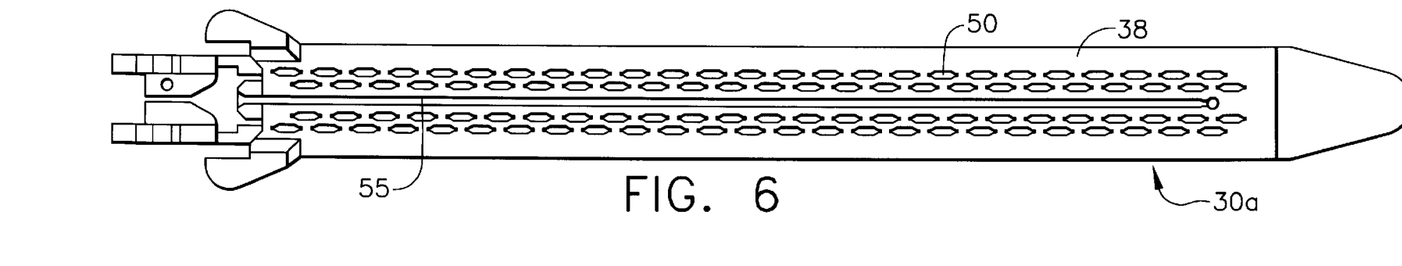
FIG. 6 is a top plan view of the cartridge of FIG. 4.

As best illustrated in FIGS. 2, 5a and 5b, the cartridge 30a, according to the present invention, is a housing which includes a plurality of vertical windows or slots 35 provided in the sidewalls 34 of the cartridge 30a. Although it is depicted that the slots 35 extend completely through the sidewalls 34, it is well within the scope of the present invention to provide slots 35 in the sidewalls 34 that would not extend completely through the sidewalls 34. Accordingly, it is not outside of the scope of the present invention to include slots 35 that are not open windows, but rather grooves formed in the sidewalls 34. It is preferable, however, that the present invention utilize slots 35 that are open windows that extend entirely through sidewalls 34.

Figure 7:
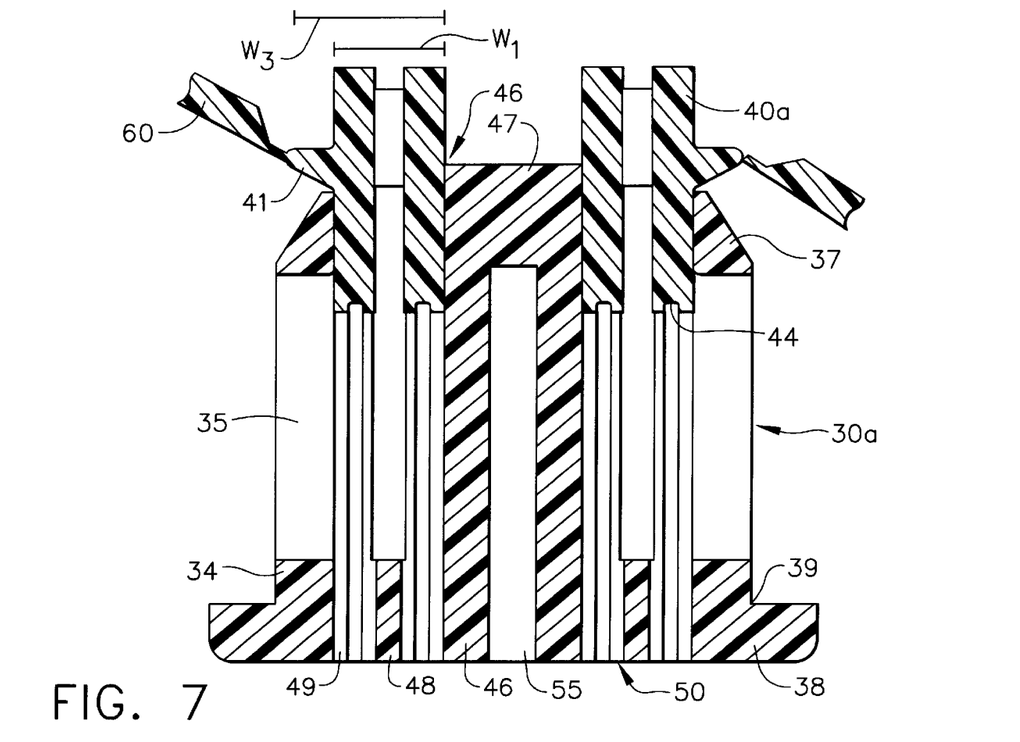
FIG. 7 is a transverse sectional view of the cartridge of FIG. 4 illustrating the initial insertion of a plurality of drivers attached to a molding sprue wherein the right side of the figure illustrates the molding sprue being separated from a driver.

As illustrated in FIG. 7, the cartridge 30a includes drivers 40a having a projection or tab 41 which laterally extends from the drivers 40a. As clearly illustrated, tabs 41 extend laterally from the drivers 40a and define a driver width $W_3$ that is larger than the cavity width $W_1$. A sprue 60 is detachably connected to the tab 41 for assisting in the loading of the drivers 40a into the driver cavities 36. Through the use of the sprue 60, a series of drivers 40a can be aligned in linear fashion utilizing the sprue 60 to interconnect an entire row of drivers 40a. Accordingly, an entire row of drivers 40a can be loaded into the driver cavity 36 at one time. This eliminates the need to hand load all of the drivers 40a one at a time which is common in the loading of the prior art cartridge 30 (FIG. 3). Since the sprue 60 is detachably connected to the driver tabs 41, the sprue 60 can be broken away or detached from the tab 41 at the time of loading.

Figure 9:
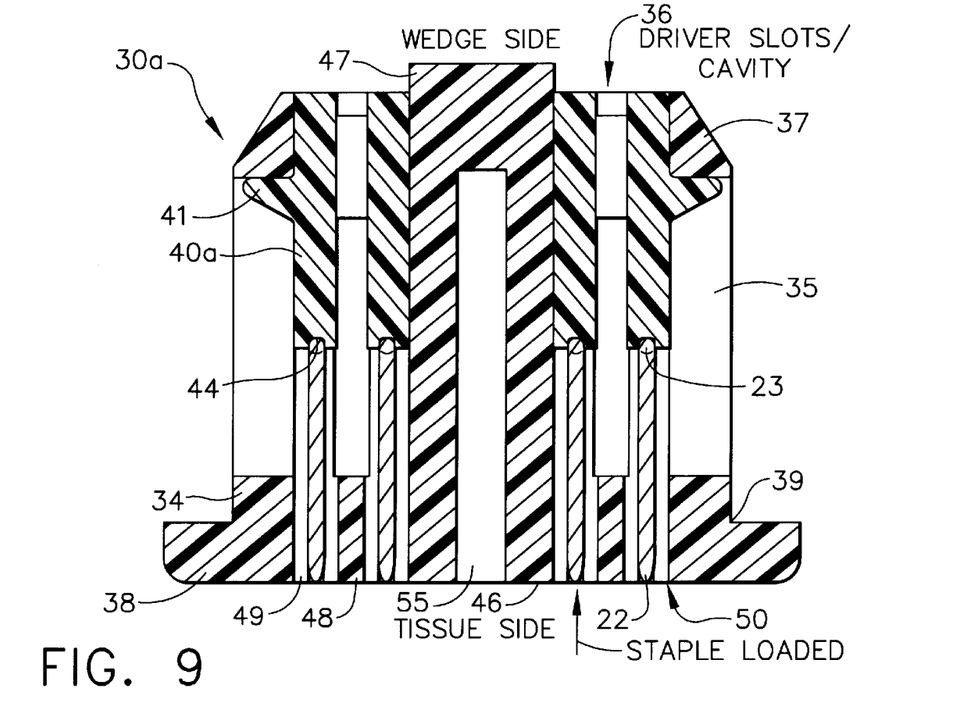
FIG. 9 is a transverse sectional view of the cartridge of FIG. 4 illustrating the fasteners and drivers in a pre-fire position.
Figure 10:
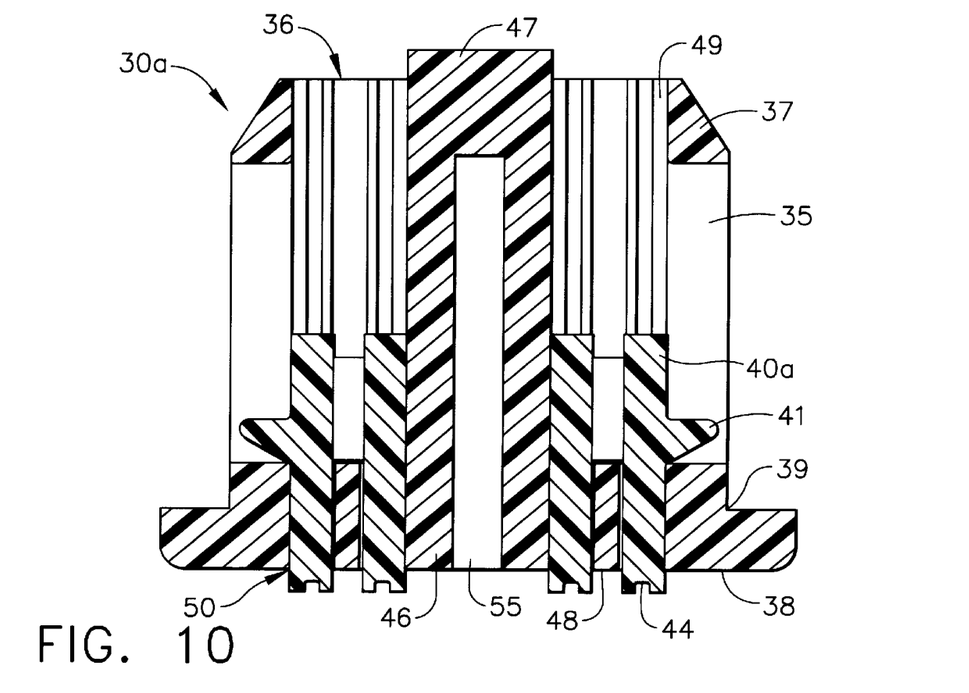
FIG. 10 is a transverse sectional view of the cartridge of FIG. 4 illustrating the drivers in their fired position.

The slots 35 of the sidewalls 34 are sized to sufficiently accommodate the tabs 41 of the drivers 40a such that the tabs 41 are movably confined within the slots 35 as best illustrated in FIGS. 9–10.

Present Invention Cartridge Manufacturing Method

As best illustrated in FIGS. 7–10, the method for manufacturing the cartridge 30a according to the present invention, includes placing the surface member 38 on a flat surface such that the main rib distal end 47 is in a superior position. Next, the drivers 40a are placed into the driver cavities 36 up until the tabs 41 rest against the distal ends 37 of the sidewalls 34. As mentioned above, the sprue 60 allows for an entire row of drivers 48 to be located simultaneously in the cavity 36 for easy loading.

Once the driver tabs 41 are positioned against the distal ends 37 of the cartridge sidewalls 34, the sprue 60 is detached or broken away from the tabs 41 as best shown on the right hand side of FIG. 7.

Figure 8:
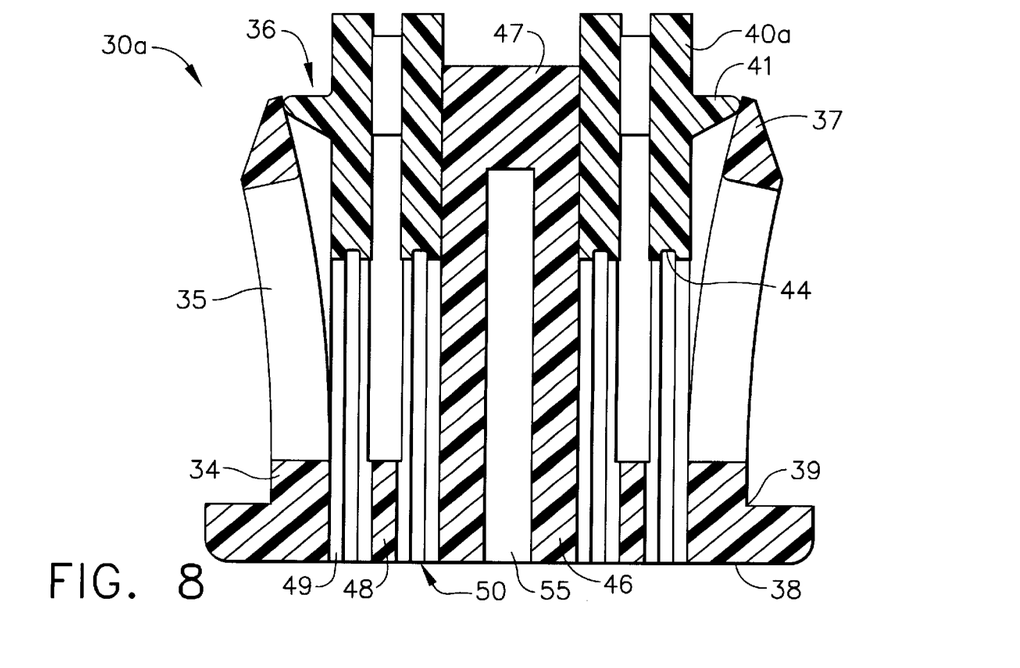
FIG. 8 is a transverse sectional view of the cartridge of FIG. 4 illustrating a forced insertion of the drivers into the cartridge.

As shown in FIG. 8, the sidewalls 34 are then deflected outwardly from the main rib 47 by depressing the drivers 40a into the cavities 36. By applying a slight force to the drivers 48, the tabs 41 contact the inner surface of the sidewall distal ends 37 and slidably move against the distal ends 37 as the sidewalls 34 are deflected outwardly from the cartridge 30a.

Once the tabs 41 move past the distal ends 37 of the sidewalls 34, the tabs 41 enter directly into the sidewall slots 35 as depicted in FIGS. 9–10. Cartridge 30a is made of a plastic material that is sufficient enough to withstand the slight force applied by the drivers 40a against the sidewalls 34 as the drivers 40a are depressed into the driver cavities 36. The material composition of the sidewalls 34, permit the sidewalls 34 to be deflected outwardly away from the cartridge 30a in order to accommodate the drivers 40a which are inserted in a press-fit manner.

On the other hand, it is not outside the scope of the present invention to alternatively utilize drivers 40a with tabs 41 that are made of a flexible material and cartridge side walls 34 that are rigid so long as the drivers 40a can be press-fit into the driver cavities 36 and the tabs 41 are insertable into the side wall slots 35.

Once the drivers 40a are press-fit into the driver cavities 36 such that the driver tabs 41 reside within the sidewall slots 35, the tabs 41 are movably confined within the slots 35. The movable confinement of the tab 41 within the slot 35 permits the driver 40a to move within the cavity 36 in a predictable manner, yet still be retained in the cartridge 30a. Because the width $W_3$ of the driver 40a is greater than the width $W_1$ of the driver cavity 36, there is little danger of the driver 40a falling out of the cartridge 30a during shipping, handling or usage once the driver tab 41 resides within the slot 35 of the sidewall 34.

The driver slots 35 are dimensioned such that they permit for a predetermined movement range of the drivers 40a within the cavity 36 by confining the tabs 41 within a predetermined movement range. By movably confining the tabs 41 within the sidewall slots 35, the predetermined movement range can be accurately determined. Thus, depending on the desired distance for advancing the drivers 40a, the cartridge 30a can be manufactured to specifications in a relatively easy and controllable manner.

The next step in the manufacturing method according to the present invention is to load the staples 22 into the cartridge 30a such that the staple crown 23 is located in the driver grooves 44 once the staples 22 are placed in the cartridge 30a through the pockets 50.

The configuration and manufacturing method of the cartridge 30a according to the present invention eliminates the expensive pressing tool 28 associated with the prior art cartridge 30 (FIG. 3). As mentioned above, the pressing tool 28 is usually a heat staking device that is difficult to maintain and control due to the amount of variables that are built into manufacturing of the prior art cartridges 30.

Since the cartridge 30a according to the present invention eliminates the need for the pressing tool 28, there are significant cost savings associated with the manufacturing method according to the present invention due to the elimination of the pressing tool 28 as well as the reduction of the labor required to manage and operate the tool 28. Moreover, there is a great reduction in cartridge scrap due to the novel and efficient method for manufacturing the cartridge 30a according to the present invention.

Present Invention Cartridge Firing

As best illustrated in FIG. 5a, the driver tabs 41 are located in the slots 35 in a pre-fire position, e.g. a position prior to the instrument 20 (FIG. 1) being fired. Upon firing of the instrument 20, the drivers 40a are advanced toward the surface member 38 to a fired position as illustrated in FIG. 5b. Throughout this firing sequence, the tab 41 is movably confined within the slot 35 thereby eliminating any chance of an overdrive of the driver 40a. The elimination of any potential overdrive is best illustrated in FIG. 10 whereby the driver 40a is shown to be advanced through the pocket 50 at a predetermined distance or up until the driver tab 41 engages the surface member 38. Accordingly, the cartridge 30a and manufacturing method thereof according to the present invention is novel, cost effective and predictable. Its predictability allows it to be a reliable disposable cartridge for use in a high precision surgical instrument 20 such as those mentioned above.

Although this invention has been described in connection with its most preferred embodiments, it will become readily apparent to those reviewing this detailed specification that numerous additional embodiments fall well within the scope and spirit of the claimed invention as set forth in the claims which appear below.

What is claimed is:

1. A surgical instrument cartridge comprising:
   a housing including a surface member and a pair of sidewalls spaced a distance apart from each other and connected to said surface member, wherein at least one of said sidewalls has at least one slot therethrough; and
   at least one driver having a tab, said driver being movable with resect to said at least one sidewall such that said tab is movable within said at least one slot.

2. The cartridge according to claim 1, wherein said surface member of said housing includes at least one pocket therein and aligned with said at least one driver.

3. The cartridge according to claim 2, including at least one staple associated with said at least one driver.

4. The cartridge according to claim 3, wherein said at least one driver is movable with respect to said at least one sidewall from a pre-fire position to a fired position.

5. The cartridge according to claim 1, wherein said at least one sidewall is deflectable.

6. The cartridge according to claim 1, including a sprue detachably connected to said tab of said at least one driver.

7. The cartridge according to claim 1, wherein said tab is movably confined within said at least one slot.

8. A surgical instrument cartridge comprising:
   a housing including a surface member and a pair of sidewalls spaced a distance apart from each other and connected to said surface member, wherein at least one sidewall is deflectable; and
   at least one driver having a tab, said driver being insertable into said cartridge upon deflection of said at least one sidewall.

9. The cartridge according to claim 8, wherein said at least one sidewall includes a slot therein.

10. The cartridge according to claim 9, wherein said tab of said at least one driver is movably confined within said slot.

11. The cartridge according to claim 10, wherein said surface member of said housing includes at least one pocket therein and aligned with said at least one driver.

12. The cartridge according to claim 11, including at least one staple associated with said at least one driver.

13. A method for manufacturing a surgical instrument cartridge comprising:
    providing a cartridge comprising a housing including a surface member and a pair of sidewalls spaced a distance apart from each other and connected to said surface member, wherein at least one of said sidewalls has at least one slot therein;

deflecting said at least one sidewall having said at least one slot;

placing a driver having a tab adjacent said deflected at least one sidewall by inserting said tab into said slot such that said driver is movable with respect to said at least one sidewall and said tab is movably confined within said slot.

14. The method according to claim 13, including locating a staple on said driver.

15. A method for manufacturing a surgical instrument cartridge comprising:

providing a cartridge comprising a housing including a surface member and a pair of sidewalls spaced a distance apart from each other and connected to said surface member wherein at least one of said sidewalls has a plurality of slots arranged therein;

deflecting said at least one sidewall;

placing a plurality of drivers wherein each driver has a tab adjacent said deflected at least one sidewall; and inserting said tab of each driver in each slot of said deflected at least one sidewall such that each driver is movable with respect to said at least one sidewall and each tab is movably confined within each slot.

16. The method according to claim 15, including locating a staple on each driver.

17. A method for manufacturing a surgical instrument cartridge comprising:

providing a cartridge comprising a housing including a surface member and a pair of sidewalls spaced a distance apart from each other and connected to said surface member, wherein at least one of said sidewalls has at least one slot therein;

deflecting said at least one sidewall; and placing a driver having a tab into said housing at said at least one sidewall by inserting said tab into said at least one slot.

18. The method according to claim 17, including locating a staple on said driver.

19. A method for manufacturing a surgical instrument cartridge comprising:

providing a cartridge comprising a housing including a surface member and a pair of sidewalls spaced a distance apart from each other and connected to said surface member, wherein at least one sidewall is deflectable; and movably engaging a driver having a tab with said at least one sidewall by deflecting said at least one sidewall to position said driver adjacent said at least one sidewall.

20. The method according to claim 19, including locating a staple on said driver.

21. A surgical instrument cartridge comprising:

a housing including a surface member and a pair of sidewalls spaced a distance apart from each other and connected to said surface member wherein said sidewalls and said surface member define at least one cavity therebetween, said at least one cavity having a cavity width; and at least one driver having a driver width wherein said driver width is greater than said cavity width, and said driver being insertable into said cavity.

22. The cartridge according to claim 21, wherein at least one of said sidewalls includes at least one slot therein.

23. The cartridge according to claim 22, wherein said at least one driver includes a tab, said tab being insertable and movably confined within said at least one slot.

24. The cartridge according to claim 23, wherein said at least one sidewall is deflectable.

25. The cartridge according to claim 24, including a staple associated with said at least one driver.

* * * * *